(12) United States Patent
Farida et al.

(10) Patent No.: US 11,220,487 B2
(45) Date of Patent: Jan. 11, 2022

(54) PROCESS FOR PREPARING 3,4-DICHLORO-N-(2-CYANOPHENYL)-5-ISOTHIAZOLECARBOXAMIDE

(71) Applicant: BAYER AKTIENGESELLSCHAFT, Leverkusen (DE)

(72) Inventors: Taraneh Farida, Pulheim-Geyen (DE); Martin Littmann, Leverkusen (DE); Daniel Hartmann, Inden (DE); Kyra Larissa Pabst, Cologne (DE); Ali Sanli, Leverkusen (DE)

(73) Assignee: BAYER AKTIENGESELLSCHAFT, Leverkusen (DE)

(*) Notice: Subject to any disclaimer, the term of this patent is extended or adjusted under 35 U.S.C. 154(b) by 66 days.

(21) Appl. No.: 16/619,925

(22) PCT Filed: Jun. 11, 2018

(86) PCT No.: PCT/EP2018/065331
§ 371 (c)(1),
(2) Date: Dec. 5, 2019

(87) PCT Pub. No.: WO2018/228984
PCT Pub. Date: Dec. 20, 2018

(65) Prior Publication Data
US 2020/0140401 A1    May 7, 2020

(30) Foreign Application Priority Data

Jun. 14, 2017    (EP) .................................. 17176018

(51) Int. Cl.
C07D 275/03    (2006.01)
C07B 43/08    (2006.01)

(52) U.S. Cl.
CPC ............ C07D 275/03 (2013.01); C07B 43/08 (2013.01)

(58) Field of Classification Search
CPC ............................. C07B 43/08; C07D 275/03
See application file for complete search history.

(56) References Cited

U.S. PATENT DOCUMENTS

| | | | |
|---|---|---|---|
| 5,939,561 A * | 8/1999 | Bourzat | C07D 205/08 548/953 |
| 6,277,791 B1 | 8/2001 | Assmann et al. | |
| 6,372,692 B1 | 4/2002 | Assmann et al. | |
| 6,642,181 B2 | 11/2003 | Assmann et al. | |
| 6,875,783 B2 | 4/2005 | Assmann et al. | |
| 7,157,481 B2 | 1/2007 | Assmann et al. | |
| 7,696,355 B2 | 4/2010 | Assmann et al. | |
| 2004/0167194 A1 * | 8/2004 | Randall | C07D 235/06 514/394 |

FOREIGN PATENT DOCUMENTS

| | | | |
|---|---|---|---|
| CN | 103936622 | * | 5/2014 |
| DE | 2115624 A | | 10/1972 |
| DE | 2115625 A | | 10/1972 |
| EP | 3072943 | * | 9/2016 |
| JP | 2009280545 | * | 12/2009 |
| WO | 99/24413 A2 | | 5/1999 |
| WO | 2004/002968 A1 | | 1/2004 |
| WO | WO 2004/002968 | * | 1/2004 |
| WO | 2007/031146 A1 | | 3/2007 |
| WO | WO2007/031146 | * | 3/2007 |
| WO | WO 2007/065655 | * | 6/2007 |
| WO | WO2010/130034 | * | 11/2010 |
| WO | WO 2012/052829 | * | 4/2012 |

OTHER PUBLICATIONS

Mao (Organic Process Research & Development 2009, 13, 1206-1208).*
Krynitsky (Organic Syntheses, Coll. vol. 4, p. 436 (1963).*
Browne (J. Med. Chem. 1991, 34, 725-736).*
Meyer (J. Med. Chem. 2000, 43, 1586-1603).*
International Search Report of international Patent Application No. PCT/EP2018/065331 dated Jul. 12, 2018.

* cited by examiner

*Primary Examiner* — Valerie Rodriguez-Garcia
(74) *Attorney, Agent, or Firm* — McBee Moore & Vanik IP, LLC

(57) ABSTRACT

The present invention relates to a novel process for preparing and isolating 3,4-dichloro-N-(2-cyanophenyl)-5-isothiazolecarboxamide (Isotianil), which can be used as an active compound with microbicidal properties, wherein the amount of waste materials—e.g. solvents and diluents—is significantly reduced and the process meets the requirements of industrial scale production, in particular that it provides the product in high yield, high purity, i.e. minimum amount of by-products and impurities, and can be carried out with tolerable corrosivity in industrial scale metal, in particular stainless steel, vessels or Cr—Ni—Mo alloy pressure filters or centrifuges.

20 Claims, No Drawings

PROCESS FOR PREPARING 3,4-DICHLORO-N-(2-CYANOPHENYL)-5-ISOTHIAZOLECARBOXAMIDE

CROSS-REFERENCE TO RELATED APPLICATIONS

This application is a National Stage entry of International Application No. PCT/EP2018/065331, filed 11 Jun. 2018, which claims priority to European Patent Application No. 17176018.4, filed 14 Jun. 2017.

BACKGROUND

Field

The present invention relates to a novel process for preparing and isolating 3,4-dichloro-N-(2-cyanophenyl)-5-isothiazolecarboxamide (Isotianil), which can be used as an active compound with microbicidal properties, wherein the amount of waste materials—e.g. solvents and diluents—is significantly reduced and the process meets the requirements of industrial scale production, in particular that it provides the product in high yield, high purity, i.e. minimum amount of by-products and impurities, and can be carried out with tolerable corrosivity in industrial scale metal, in particular stainless steel, vessels or Cr—Ni—Mo alloy pressure filters or centrifuges.

Description of Related Art

Synthesis of Isotianil has been described in several patent application, for example, it is known that 3,4-dichloro-N-(2-cyanophenyl)-5-isothiazolecarboxamide (Isotianil) of the general formula (I)

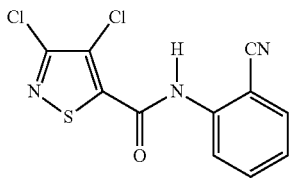

is obtained when 3,4-dichloroisothiazole-5-carbonyl chloride is reacted with 2-cyanoaniline (cf. WO 99/24413). This process has the disadvantages that the 2-cyanoaniline required as starting material can only be obtained by complicated syntheses (cf. DE-A 2 115 624 and DE-A 2 115 625), as well as
that the product has to be isolated by complicated work-up methods (cf. Example 1 of WO 99/24413).

Further, it is known that 3,4-dichloro-N-(2-cyanophenyl)-5-isothiazolecarboxamide is obtained by
a) reacting 3,4-dichloroisothiazole-5-carbonyl chloride of the formula (II)

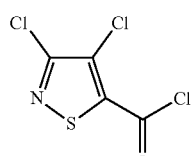

with anthranilamide of the formula (III)

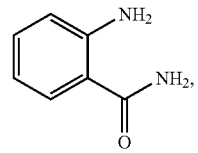

in the presence of an acid acceptor and in the presence of an aprotic diluent and
b) then reacting the N-[2-(aminocarbonyl)phenyl]-3,4-dichloro-5-isothiazolecarboxamide of the formula (IV) formed

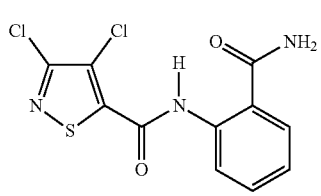

with a dehydrating agent, if appropriate in the presence of an additional aprotic diluent (cf. WO 2004/002968).

In WO 2007/031146 a process for the synthesis of Isotianil (I) is described, which provides good yields and improved purity when methyl acetate, ethyl acetate or mixtures thereof are used as solvent in the process, wherein Isotianil is obtained from the same starting materials as set forth in WO 99/24413.

However, the use of the diluents mentioned above also entails various disadvantages. Thus, chlorinated hydrocarbons, such as dichloromethane, chloroform, carbon tetrachloride, dichloroethane or trichloroethane are solvents which, owing to their toxic potential, can only be handled at relatively high technical expenditure and, moreover, the amount of waste materials is significantly increased. According to the teaching of WO 2007/031146 there is an increased formation of N-[2-(N'-formylaminocarbonyl)phenyl]-3,4-dichloro-5-isothiazolecarboxamide of the formula (V)

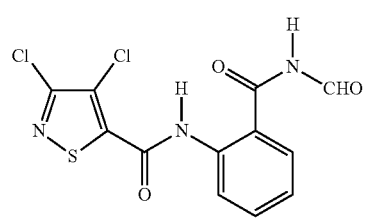

as unwanted by-product which contaminates the product, if the reaction is carried out in halogenated aromatic hydrocarbons, such as toluene or chlorobenzene. Moreover, the reaction in these diluents requires increased amounts of dehydrating agents.

Further, the use of dialkylamides such as dimethylformamide or dibutylformamide as solvent is disadvantageous owing to the relatively high price of these solvents.

The process according to WO 2007/031146 can be carried out as a one-pot reaction without isolation of the intermediate (IV), wherein in this favoured procedure methyl acetate, ethyl acetate or a mixture thereof is employed for the whole process.

However, in this process the filtrate contains excess Vilsmeier-reagent as well as $SO_2$ and hydrochloric acid (HCl), which are highly corrosive. On the other hand, aqueous work-up was not considered feasible, since under those conditions the N-formyl by-product is generated in significant amounts.

As shown, while in theory non-aqueous work-up and isolation of the product is possible, the reaction mixture is highly corrosive, thus, expensive, special equipment has to be used in this route, which makes the process more costly and scale-up to industrial amounts more difficult.

Accordingly, there still was a need for an improved process which allows the preparation of 3,4-dichloro N-(2-cyanophenyl)-5-isothiazolecarboxamide in good yields with comparable low amounts of the impurity N-[2-(N'-formylaminocarbonyl)phenyl]-3,4-dichloro-5-isothiazolecarboxamide of the formula (V) as well as other impurities, without using expensive diluents or diluents difficult to handle or difficult in workup or waste processing, while reducing the amount of waste per kg product.

Moreover, as pointed out above, control of the corrosive properties of the Vilsmeier-reagent in the dehydration step is an important issue. The latter in particular is of importance when scale up of the reactions is considered and steel apparatuses are used instead of glassware used in lab-scale. Hence, it was an object of the invention to reduce the amount of Vilsmeier-reagent in the reaction as well as the general reduction of waste products, since those factors have both positive economical (less costs) and ecological effects (less environmental impact).

Further, there is always need for an increase in space-time yield and process throughput.

SUMMARY

Therefore, the object of the invention is to provide a process with reduced quantity of waste material with reduced and tolerable corrosive properties, in particular when carried out in industrial scale.

The calculation of the quantity of waste material, as described above, does not only include the actual amounts of solvents, starting materials and residues, but also includes aqueous and organic phases as well as the required chemicals for there dilution and/or neutralisation or treatment before deposition or incineration.

As far as not defined otherwise in the present invention, room temperature is between 20° C. to 22° C.

Moreover, preferred ranges of different parameters are to be understood that they can be freely combined, independent of the level of preference. However, at least, the combination of all most preferred levels of each parameter are to be understood as the preferred embodiment of the total process.

According to the present invention the process for the production of Isotianil comprises the steps:

a) reacting in an organic, preferably aromatic, solvent in a first step (a) 3,4-dichloroisothiazole-5-carbonyl chloride of the formula (II)

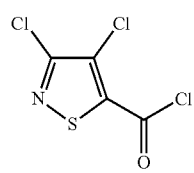

with anthranilamide of the formula (III)

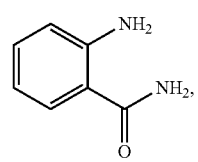

b) subsequently dehydrating in a second step (b), which is carried out as one-pot reaction, i.e. without isolation of the intermediate (IV) (N-[2-(aminocarbonyl)phenyl]-3,4-dichloro-5-isothiazolecarboxamide)

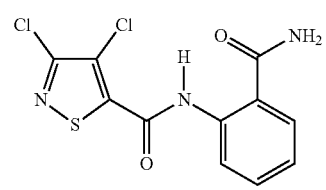

and, c) aqueous work-up with an inorganic base (quenching) (c), with optional adjustment of pH, d) degassing of the quenched reaction mixture (d), e) adjustment of pH of the reaction mixture (e), and f) filtration and isolation of the product (f).

DETAILED DESCRIPTION OF A PREFERRED EMBODIMENT

It has been found that in contrast to prior assumptions (s. above) step (c) can be carried out by quenching of the reaction with aqueous inorganic base without significant generation of unsoluble by-products in this step. Further, it has been found advantageous that the pH of the quenched mixture is adjusted, wherein it is preferably adjusted between 1.0 and 6.0, more preferred between 1.5 and 5.5, even more preferred between 1.8 and 2.2, and most preferred about between 1.9 and 2.0. Preferably, adjustment of pH is done with the same inorganic base as used in the work-up step (c).

Furthermore, in this particular process, addition of an acid acceptor (auxiliary base)—as described in the prior art—is not required, thus, the reaction is carried out without acid acceptor.

It has been found, that the required amount of solvent in the present invention is lower compared to the process described in the prior art (WO 2007/031146).

Moreover, it has been found that it is advantageously that after initial "quenching" of the reaction with an inorganic base, according to step (d), the resulting suspension is heated and stirred at this temperature for some time to remove remaining gases, in particular sulfur dioxide (SO$_2$).

In the following, when ranges are given "between" two data points, said data points should be included in the respective range.

Moreover, preferably the process steps are carried out in the sequence as indicated above, however, if applicable, the sequence of steps may be changed if necessary and chemically feasible.

Step (a)

The organic solvent is preferably selected from the group consisting of benzene, toluene, o-xylene, m-xylene, p-xylene, chlorobenzene, methyl acetate, ethyl acetate, dimethyl acetamide or the mixtures thereof. Preferably non halogenated solvents are used, in particular aromatic solvents, and more preferred the organic solvent is selected from the group consisting of toluene, o-xylene, m-xylene and p-xylene. Most preferred the organic solvent used in the instant invention is toluene.

When carrying out the process according to the invention, the temperatures can be varied within a relatively wide range.

When carrying out the process according to the invention, the temperatures during the formation of the intermediate (IV) (first process step (a)) are generally in the range between 20° C. to 160° C., preferably in the range between 50° C. to 150° C., more preferred in the range between 70° C. to 130° C., and most preferred in the range between 80° C. to 120° C. In a particular preferred embodiment the first reaction step is carried out in a range of 105° C. to 115° C.

In a most preferred embodiment, the process is carried out at or up to 10K above the boiling point of the respective solvent used in the process, e.g. for toluene up to about 121° C.

In case the reaction is carried out under reduced pressure/in vacuo, the reaction temperature is preferably adjusted to the reduced boiling point of the solvent, wherein preferably the elevation of boiling point is considered. When working under reduced pressure, the reaction temperature can be decreased and thus, a positive impact on the energy balance can be achieved. Moreover, by removing volatile reaction products under reduced pressure, the reaction equilibrium can be shifted, thus, reaction time is shortened and yield, in particular space-time-yield—is increased.

In this alternative embodiment, the first step of the reaction is carried out under reduced pressure, preferable from 10 mbar to 700 mbar, more preferred from 150 mbar to 500 mbar, even more preferred in a range from 200 mbar to 400 mbar and most preferred from 220 mbar to 280 mbar, in particular when toluene is used as a solvent, wherein the range—as in the following—gives the actual pressure and not the reduction of pressure compared to normal pressure. If the reaction is carried out in the range from 220 mbar to 280 mbar, reaction temperature is preferably between 75° C. to 90° C.

However, depending on the absolute pressure and the solvent used in the process, the skilled artisan will adjust temperature and pressure in a way that the boiling point of the solvent under the chosen conditions is reached. However, to achieve acceptable reaction times as well as safe reaction conditions (e.g. not too many side products by thermal decomposition) the reaction temperature is generally between 40° C. and 160° C., while for economic reasons (energy consumption, recovery of solvent, etc.) the reduce pressure is usually applied in a range from 150 mbar to 500 mbar.

The advantage of carrying out the reaction under reduced pressure is a faster reaction—at the same temperature compared to normal pressure—, higher space-time-yield and lower energy use. On the other hand, when carrying out step (a) of the reaction under reduced pressure, care has to be taken to recover the solvent in a suitable trap, wherein in particular recovery of solvent at pressures below 10 mbar is significantly more difficult. Further, efforts have to be made to seal all vessels,
and with reduced pressure and reduced boiling temperature of the solvent the reaction rate might decrease and lead to non-feasible reaction times.

Step (b)

The subsequent dehydration (step (b)) is carried out in the presence of a dehydrating agent, wherein second process step in the present case does not mean a separate process step after workup, but rather the second reaction step in the one-pot reaction.

When carrying out step (b) of the process according to the invention, the temperatures in the step (b) are generally in the range between 0 to 40° C., preferably in the range between 8 to 40° C., more preferred in the range between 10 to 35° C., and most preferred in the range between 15 to 35° C. In a particular preferred embodiment the second reaction step is carried out in a range of 16 to 30° C.

Suitable dehydrating agents are, preferably, reagents selected from the group consisting of mixtures of dialkylformamide, in particular dimethylformamide (DMF) and dibutylformamide (DBF), with thionyl chloride, phosphorus oxychloride, phosgene and/or chloromethylenedimethylammonium chloride. Preferably a mixture of dimethylformamide or dibutylformamide and thionyl chloride or phosgene as dehydrating agent, and most preferred a mixture of dimethylformamide with thionyl chloride is used.

The amounts of phosgene or thionyl chloride employed when carrying out the process according to the invention are generally between 1.0 and 2.5 mol per mole of 3,4-dichloroisothiazole-5-carbonyl chloride, preferably between 1.0 and 2.0 mol per mole of 3,4-dichloroisothiazole-5-carbonyl chloride, more preferred between 1.0 and 1.5 mol per mole of 3,4-dichloroisothiazole-5-carbonyl chloride, and most preferred between 1.0 and 1.3 mol per mole of 3,4-dichloroisothiazole-5-carbonyl chloride.

The amounts of dialkylformamide employed when carrying out the process according to the invention are between 1.0 and 8.0 mol per mole of 3,4-dichloroisothiazole-5-carbonyl chloride, preferably between 2.0 and 6.0 mol per mole of 3,4-dichloroisothiazole-5 carbonyl chloride, more preferred between 3.0 and 5.0 mol per mole of 3,4-dichloroisothiazole-5 carbonyl chloride, even more preferred between 4.0 and 5.0 mol per mole of 3,4-dichloroisothiazole-5 carbonyl chloride, and most preferred between 4.3 and 4.7 mol per mole of 3,4-dichloroisothiazole-5 carbonyl chloride.

In a more preferred embodiment the dehydrating step is carried out with an amount between 1.0 and 1.5 mol per mole of 3,4-dichloroisothiazole-5-carbonyl chloride of thionyl chloride and an amount between 4.3 and 4.7 mol per mole of 3,4-dichloroisothiazole-5 carbonyl chloride of dimethylformamide.

As pointed out before, when carrying out the process according to the invention, both the reaction in the first step (a) and in the second step (b) can be carried out under atmospheric pressure.

However, in an alternative embodiment it is preferred to operate under reduced pressure, preferably at about 250 mbar at a temperature between 83° C. to 88° C. in step (a), wherein toluene is used as a solvent.

The reaction times for carrying out the process according to the invention are generally between 1 and 24 hours and depend essentially on the reaction temperature and the choice and amount of the dehydrating agent used in each case, as well as scale. Preferred reaction times are between 1 and 12 hours, more preferred between 2 and 10 hours, and most preferred between 3 and 8 hours wherein "reaction time" refers to each of the reaction steps (a) and (b) separately, although the reaction is carried out as one-pot reaction.

Step (c)

In an embodiment of the process of the present invention work-up (c) includes addition of the reaction mixture to an aqueous base, preferably a carbonate or a hydroxide of an alkali or earth alkali metal. More preferred, the base is selected from sodium carbonate, potassium carbonate, sodium hydroxide, potassium hydroxide, and even more preferred are potassium and sodium hydroxide. Most preferred is the use of sodium hydroxide which not only has the economic advantage of low costs, but also has no negative impact on carbon dioxide emissions.

The amount of base employed in the initial work-up step (c) is between 0.5 and 4.0 mol per mole of thionyl chloride, preferably between 1.0 and 3.0 mol per mole of thionyl chloride, even more preferred between 1.5 and 2.5 mol per mole of thionyl chloride and most preferred between 1.8 and 2.2 mol per mole of thionyl chloride.

The resulting pH of the quenched mixture can be adjusted, wherein it is preferably adjusted between 1.0 and 6.0, more preferred between 1.5 and 5.5, even more preferred between 1.8 and 2.2, and most preferred about between 1.9 and 2.0.

In the best mode the pH is adjusted to 1.9 to 2.0.

Preferably, the reaction mixture is added to the base solution, which was cooled to −5° C. to 10° C., more preferred to 0° C. to 10° C., and most preferred to 0° C.

Preferably, the base is added as aqueous solution, preferably a concentrated or saturated aqueous solution of the base, e.g. 32% sodium hydroxide solution in a best mode embodiment.

The reaction mixture is added to the base under temperature control, wherein the temperature is allowed to increase up to 16° to 60° C., preferably up to 45° C. to 60° C., and most preferred up to 55° C. Depending on the temperature, the addition process may be expedited or take longer as long as the temperature is kept in the specified range, wherein preferably mixture is added over a period of time of 2 hours.

After complete addition, the mixture is heated to 55° C. and held at that temperature for degassing.

It is also possible to add the base to the reaction mixture in a "reversed" alternative method, wherein the same temperature requirements apply.

Optionally, with or after addition of the base, up to 33 mol water per mole of 3,4-dichloroisothiazole-5 carbonyl chloride, preferably from 10 to 25 mol water per mole of 3,4-dichloroisothiazole-5 carbonyl chloride, and most preferred 20 to 25 mol water per mole of 3,4-dichloroisothiazole-5 carbonyl chloride may be added to allow precipitating salts to dissolve.

Further, in another embodiment, the reaction mixture is added to the base under temperature control, wherein the temperature is kept in the range from 0° C. to 25° C., preferably from 10° C. to 25° C. and most preferred from 18° C. to 23° C. After complete addition, the mixture is heated to 55° C. and subsequently treated like described above.

Step (d)

In a further step (d) (degassing) volatile reaction products are removed from the reaction mixture by degassing, wherein preferably acidic volatile components like sulfur dioxide and hydrochlorid acid are removed.

The advantage of outgassing the acidic volatile compounds like sulfur dioxide is in lower cost for subsequent waste water treatment, since significant lower amounts of base have to be used to adjust pH for filtration, resulting in less waste water.

Degassing (d) preferable is carried out over a period of 0.5 h to 5.0 h, more preferred over a period of 1.0 h to 4.0 h, and most preferred over a period of 2.0 to 4.0 h Further, step (d) is carried out at a temperature in the range of to 50° C. to 60° C., preferably 55° C.

Moreover, step (d) is preferable carried out under reduced pressure at the temperatures given above, wherein the same ranges as under steps (a) and (b) apply.

Step (e)

After first neutralisation of the reaction mixture (c) and degassing (d), the temperature is adjusted to 18° C. to 25° C., preferably to 20° C. to 22° C., or room temperature, and then the pH is adjusted to a pH in the range between 5 and 7, preferably 5 and 6, and most preferred about 5, to further minimize corrosivity of the mixture. pH can be measured, e.g., by an electrode in a closed pump circuit.

The base used for pH adjustment is preferably the same base used in the foregoing first neutralisation, therefore, sodium hydroxide (in solution) is most preferred.

The precipitated product is filtered off, preferably by vacuum suction.

Further preferred, the precipitate is washed, wherein even more preferred the precipitate is washed at least once with water and at least once with an organic solvent.

The organic solvent can be a solvent used in the reaction or selected from the group of methanol, ethanol, and propanol. Most preferred, the organic solvent used for washing is methanol.

With the processes of the present invention the amount of waste per kg product can be reduced from about 18 kg waste per kg product generated in the current technical process using methylacetate procedure with aqueous work-up as described in WO 2007/031146 to 10 kg waste per kg product or less according to the present invention. In particular, the amount of aqueous waste is reduced by half from about 12 kg per kg product to 6 kg, whereas the amount of organic waste is even reduced nearly by a factor of 3 (2.84) from about 7.1 kg per kg product to 2.5 kg.

In the above the amount of waste is calculated based on DCIT acid as starting material with an estimated average yield of the overall reaction of 85%.

Due to the process according to the present invention and the waste reduction costs for solvents as starting materials as well as for waste disposal and treatment are significantly lowered. Moreover, in particular with removal of $SO_2$ and an adjustment of pH to about 5 before filtration, corrosivity is significantly reduced and less expensive materials for vessel and filters can be used, while the lifetime is extended.

The process according to the invention is distinguished by a number of advantages. It permits the preparation of 3,4-dichloro-N-(2-cyanophenyl)-5-isothiazolecarboxamide in very good yield and high purity with reduced costs due to cheaper solvents, less material (auxiliary base), easier work-up and less waste material per kg product, wherein the latter also has a strong ecological impact.

Without any problems, the process according to the invention can be carried out on an industrial scale, among other reasons, due to reduced corrosivity.

In a preferred embodiment of the present invention the process for the production of Isotianil comprises the steps:
a) reacting in an organic solvent in a first step (a) 3,4-dichloroisothiazole-5-carbonyl chloride of the formula (II)

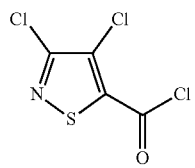

(II)

with anthranilamide of the formula (III)

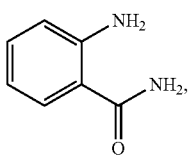

(III)

b) subsequently dehydrating in a second step (b), which is carried out as one-pot reaction, i.e. without isolation of the intermediate (IV) (N-[2-(aminocarbonyl)phenyl]-3,4-dichloro-5-isothiazolecarboxamide)

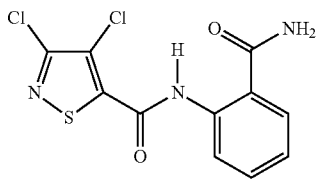

(IV)

and,
c) aqueous work-up with an inorganic base (quenching) (c), with optional adjustment of pH,
d) degassing of the quenched reaction mixture (d),
e) adjustment of pH of the reaction mixture (e), and
f) filtration and isolation of the product (f),
wherein the organic aromatic solvent is selected from the group consisting of benzene, toluene, o-xylene, m-xylene and p-xylene, preferably toluene, and,
Step (a) is carried out in a range of 105-115° C., and
Step (b) of the one-pot reaction is carried out in the presence of a dehydrating agent in a range of 16° C. to 30° C.,
wherein the dehydrating agent is a mixture of dimethylformamide and thionylchloride,
wherein the amount of thionyl chloride is between 1.0 and 1.5 mol per mole of 3,4-dichloroisothiazole-5-carbonyl chloride, and preferably between 1.0 and 1.3 mol per mole of 3,4-dichloroisothiazole-5-carbonyl chloride, and
wherein the amount of dimethylformamide is between 4.0 and 5.0 mol per mole of 3,4-dichloroisothiazole-5-carbonyl chloride, preferably between 4.3 and 4.7 mol per mole of 3,4-dichloroisothiazole-5 carbonyl chloride, and in Step (c) work-up (c) includes addition of a 32% solution of sodium hydroxide, wherein the amount of base is between 1.8 and 2.2 mol per mole of thionyl chloride, wherein the pH after quenching is between 1.8 and 2.2, preferably about 2.0, or, alternatively, the pH is adjusted to said pH, and
wherein the reaction mixture is added to the base over a period of time of 2 hours under temperature control, wherein the temperature is allowed to increase up to 50° C. to 60° C., preferably 55° C., and
wherein in Step (d) volatile reaction products are removed from the reaction mixture by degassing over a period of 2 to 4 h at 55° C., and
wherein in Step (e), the temperature is adjusted to 20° C. to 22° C. and then the pH is adjusted to a pH in the range between 5 and 6 with a 32% solution of sodium hydroxide, and wherein the precipitated product is filtered off, preferably by pressure filter (or vacuum suction), and washed with water and methanol.

In an alternative embodiment to the preceding reaction, the reaction mixture is added to the base over a period of time of 2 hours under temperature control, wherein the temperature is kept between 0° C. and 25° C., while subsequent degassing takes place at 55° C. as described above.

In another preferred embodiment of the present invention the process for the production of Isotianil under reduced pressure in steps a) and d) comprises the steps:
a) reacting in an organic solvent in a first step (a) 3,4-dichloroisothiazole-5-carbonyl chloride of the formula (II)

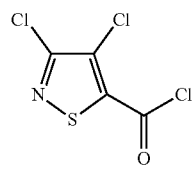

(II)

with anthranilamide of the formula (III)

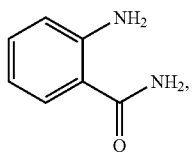

(III)

b) subsequently dehydrating in a second step (b), which is carried out as one-pot reaction, i.e. without isolation of the intermediate (IV) (N-[2-(aminocarbonyl)phenyl]-3,4-dichloro-5-isothiazolecarboxamide)

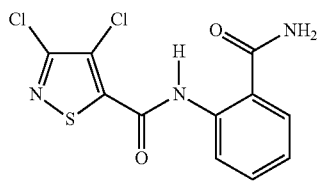

(IV)

and,
c) aqueous work-up with an inorganic base (quenching) (c), with optional adjustment of pH, d) degassing of the quenched reaction mixture (d),
e) adjustment of pH of the reaction mixture (e), and
f) filtration and isolation of the product (f),
wherein the organic aromatic solvent is selected from the group consisting of benzene, toluene, o-xylene, m-xylene and p-xylene, preferably toluene, and,
wherein the reaction is carried out under reduced pressure in the range from 220 mbar to 280 mbar, and
wherein reaction temperature is preferably between 83° C. to 88° C., and
wherein Step (b) of the one-pot reaction is carried out in the presence of a dehydrating agent in a range of 16° C. to 30° C.,
wherein the dehydrating agent is a mixture of dimethylformamide and thionylchloride,
wherein the amount of thionyl chloride is between 1.0 and 1.5 mol per mole of 3,4-dichloroisothiazole-5-carbonyl chloride, and preferably between 1.0 and 1.3 mol per mole of 3,4-dichloroisothiazole-5-carbonyl chloride, and
wherein the amount of dimethylformamide is between 4.0 and 5.0 mol per mole of 3,4-dichloroisothiazole-5 carbonyl chloride, preferably between 4.3 and 4.7 mol per mole of 3,4-dichloroisothiazole-5 carbonyl chloride, and
in step (c) work-up (c) includes addition of a 32% solution of sodium hydroxide, wherein the amount of base is between 1.8 and 2.2 mol per mole of thionyl chloride, wherein the pH after quenching is between 1.8 and 2.2, preferably about 2.0, or, alternatively, the pH is adjusted to said pH, and
wherein the reaction mixture is added to the base over a period of time of 2 hours under temperature control, wherein the temperature is allowed to increase up to 50° C. to 60° C., preferably 55° C., and
wherein in Step (d) volatile reaction products are removed from the reaction mixture by degassing over a period of 2-4 h at 55° C., and
wherein in Step (e), the temperature is adjusted to 20° C. to 22° C. and then the pH is adjusted to a pH in the range between 5 and 6 with a 32% solution of sodium hydroxide, and the precipitated product is filtered off, preferably by pressure filtration (or vacuum suction), and washed with water and methanol.

In an alternative embodiment to the preceding reaction, the reaction mixture is added to the base over a period of time of 2 hours under temperature control, wherein the temperature is kept between 0° C. and 25° C., while subsequent degassing takes place at 55° C. as described above. The examples described below illustrate the present invention in more detail; however, they do not limit the present invention. Here, the stated yields are to be understood as total yield over the combined process steps.

WORKING EXAMPLES AND COMPARATIVE EXAMPLES

Example 1

The reaction vessel is charged with 505.8 g (5.46 mol) toluene at room temperature. 190.0 g (1.37 mol) of anthranilamide are added.

Subsequently 294.2 g (1.30 mol) of 3,4-dichloroisothiazole-5-carbonyl chloride in toluene are added dropwise over a period of 3 hours at 90° C.-114° C. The mixture is stirred at 114° C. for another 4 hours under normal pressure. The mixture is cooled to 90° C. and then, while cooling, 429.9 g (5.87 mol) DMF is added dropwise over a period of 30 min.

The mixture is cooled to 18° C. and 210.6 g (1.76 mol) of thionyl chloride are then added dropwise at 18° C.-23° C. over a period of 2 hours. The mixture is stirred at 18° C.-23° C. for another 3 hours.

Work-Up 564 g (31.30 mol) of water and 477.4 g (3.82 mol) sodium hydroxide solution (32%) are charged in a reaction vessel at room temperature and then cooled to 0° C., The reaction mixture is added over 2 hours to the sodium hydroxide solution with temperature control at a temperature between 0° C. and 25° C. pH after completed addition is at pH 1.9.

The resulting suspension is heated to 55° C. over a period of 2 hours and stirred for another 4.0 hours at this temperature to remove remaining gases under reduced pressure (at appr. 200-250 mbar) at reflux, wherein.

After degassing the mixture is cooled to room temperature and pH is adjusted to 5.0 with sodium hydroxide solution (32%).

Subsequently the solid is then isolated after cooling to room temperature by filtration and washed once with water (564 g/31.3 mol) (suspension washing) and once with methanol (637 g/19.83 mol) (displacement washing) and subsequently dried in vacuo (5 mbar) at 50° C.

The isolated product has a 99.3% purity and was obtained in 91.0% yield of theory based on DCIT-chloride.

The total amount of liquid waste is about 10 kg/kg Isotianil.

Example 2

The reaction vessel is charged with 505.8 g (5.46 mol) toluene at room temperature. 190.0 g (1.37 mol) of anthranilamide are added.

Subsequently 294.2 g (1.30 mol) of 3,4-dichloroisothiazole-5-carbonyl chloride in toluene are added dropwise over a period of 3 hours at 90° C.-114° C. under normal pressure. The mixture is stirred at 114° C. for another 4 hours. The mixture is cooled to 90° C. and then, while cooling, 429.9 g (5.87 mol) DMF is added dropwise over a period of 30 min.

The mixture is cooled to 18° C. and 210.6 g (1.76 mol) of thionyl chloride are then added dropwise at 18° C.-23° C. over a period of 2 hours. The mixture is stirred at 18° C.-23° C. for another 3 hours.

Work-up 564 g (31.30 mol) of water and 477.4 g (3.82 mol) sodium hydroxide solution (32%) are charged in a reaction vessel at room temperature. The reaction mixture is added over 2 hours to the sodium hydroxide solution with temperature control at a temperature maximum of 55° C.

pH after completed addition is at pH 1.9.

The resulting suspension is heated to 55° C. over a period of 2 hours and stirred for another 4.0 hours at this temperature to remove remaining gases under reduced pressure (at appr. 200-250 mbar) at reflux.

After degassing the mixture is cooled to room temperature and pH is adjusted to 5.0 with sodium hydroxide solution (32%).

Subsequently the solid is then isolated after cooling to room temperature by filtration and washed once with water (564 g/31.3 mol) (suspension washing) and once with methanol (637 g/19.83 mol) (displacement washing) and subsequently dried in vacuo (5 mbar) at 50° C.

The isolated product has a 99.5% purity and was obtained in 90.0% yield of theory based on DCIT-chloride.

The total amount of liquid waste is about 10 kg/kg Isotianil.

Comparative Example 1

7.49 g (55 mmol) of anthranilamide, 5.57 g (55 mmol) of triethylamine and 7.31 g (100 mmol) of DMF are initially charged in 80 ml of methyl acetate. At 10-20° C., a solution of 10.83 g (50 mmol) of 3,4-dichloroisothiazole-5-carbonyl chloride in 20 ml of methyl acetate is added dropwise. The mixture is stirred at 10-20° C. for 1 hour, and 11.9 g (100 mmol) of thionyl chloride are then added dropwise at the same temperature over a period of 15 minutes. After 4 hours at 20° C., 100 ml of water are added with cooling to the reaction mixture, the mixture is stirred for 15 min and the solid is filtered off with suction and, on the Nutsche, washed with 50 ml of water and twice with in each case 20 ml of isopropanol. After drying, 13.35 g of a beige solid of the following composition are obtained:

98.1% of 3,4-dichloro-N-(2-cyanophenyl)-5-isothiazole-carboxamide (87.9% of theory)

0.4% of N-[2-(aminocarbonyl)phenyl]-3,4-dichloro-5-isothiazolecarboxamide

<0.05% of N-[2-(N'-formylaminocarbonyl)phenyl]-3,4-dichloro-5-isothiazolecarboxamide After filtration the aqueous phase is neutralized and diluted with $H_2O$ for disposal.

The total liquid waste is about 26 kg/kg Isotianil.

Comparative Example 2

0.749 g [5.5 mmol] of anthranilamide, 0.557 g (5.5 mmol) of triethylamine and 1.1 g (15 mmol) of DMF are initially charged in 8 ml of ethyl acetate. At 0° C., a solution of 1.08 g (5 mmol) of 3,4-dichloroisothiazole-5-carbonyl chloride in 2 ml of ethyl acetate is added dropwise. The mixture is stirred at 0° C. for 1 hour, and 2.38 g (20 mmol) of thionyl chloride are then added dropwise at the same temperature over a period of 15 minutes. After 2 hours at 0° C. and 2 hours at 20° C., 10 ml of water are added with cooling at 0° C. to the reaction mixture, the mixture is stirred for 15 minutes and the solid is filtered off with suction and, on the Nutsche, washed with 20 ml of water. Drying gives 1.34 g of a beige solid of the following composition:

97.2% of 3,4-dichloro-N-(2-cyanophenyl)-5-isothiazole-carboxamide (87.2% of theory)

0.2% of N-[2-(aminocarbonyl)phenyl]-3,4-dichloro-5-isothiazolecarboxamide 0.4% of N-[2-(N'-formylaminocarbonyl)phenyl]-3,4-dichloro-5-isothiazolecarboxamide After filtration the aqueous phase is neutralized and diluted with $H_2O$ for disposal.

The total liquid waste is about 33 kg/kg Isotianil.

Example 3

The reaction vessel is charged with 266.4 g (2.89 mol) toluene at room temperature.

143.3 g (1.03 mol) of anthranilamide are added.

Subsequently 244.4 g (1.01 mol/purity 89.7%) of 3,4-dichloroisothiazole-5-carbonyl chloride in 14.6 g toluene are added dropwise over a period of 2 hours at 90° C.-112° C. The mixture is stirred at 112° C. for another hour under reflux. The mixture is cooled to 90° C. and then, while cooling, 296.0 g (4.04 mol) DMF is added dropwise over a period of 30 min.

The mixture is cooled to 18° C. and 150.0 g (1.26 mol) of thionyl chloride are then added dropwise at 18° C.-23° C. over a period of 2 hours. The mixture is stirred at 18° C.-23° C. for another 3 hours.

Work-Up 432.7 g (3.46 mol) of sodium hydroxide solution (32%) are charged in a reaction vessel at room temperature and then cooled to 0° C., The reaction mixture is added over 2 hours to the sodium hydroxide solution with temperature control at a temperature between 0° C. and 25° C.

437.7 g [24.3 mol] water are added at room temperature and the mixture is stirred for 30 min. at room temperature.

pH after completed addition is at about pH 4.5. The resulting suspension is heated to 55° C. and stirred for another 1.5 hours at this temperature to remove remaining gases.

After degassing pH is adjusted to 5.0 with sodium hydroxide solution (32%). Subsequently the mixture is cooled to 20° C. and the solid is then isolated by filtration and washed once with water (437 g) (suspension washing) and once with methanol (227 g) (displacement washing) and subsequently dried in vacuo (5 mbar) at 50° C.

The isolated product has a 99.9% purity and was obtained in 90.1% yield of theory based on DCIT-chloride. After filtration the aqueous phase is neutralized and diluted with $H_2O$ for disposal.

The total liquid waste is about 12.9 kg/kg Isotianil.

Example 4

The reaction vessel is charged with 351.6 g (3.80 mol) toluene at room temperature.

186.0 g (1.34 mol) of anthranilamide are added.

Subsequently 346.8 g (1.30 mol/purity 81.2%) of 3,4-dichloroisothiazole-5-carbonyl chloride in 20.8 g toluene are added dropwise over a period of 2 hours at 85° C. at 470 mbar to 480 mbar. The mixture is stirred at at 85° C. at 470 mbar to 480 mbar for another 2 hours under reflux. The mixture is cooled to 16° C. and then, while cooling, 428.5 g (5.85 mol) DMF is added dropwise over a period of 30 min.

The mixture is cooled to 16° C. and 202.1 g (1.70 mol) of thionyl chloride are then added dropwise at 18° C.-23° C. over a period of 2 hours. The mixture is stirred at 18° C.-23° C. for another 2 hours.

Work-Up 589.8 g (4.72 mol) of sodium hydroxide solution (32%) are charged in a reaction vessel at room temperature and then cooled to 0° C., The reaction mixture is added over 2 hours to the sodium hydroxide solution with temperature control at a temperature between 0° C. and 25° C. and then stirred for another 30 min at this temperature. pH is adjusted to 5.0 with sodium hydroxide solution (32%).

The resulting suspension is heated to 55° C. and stirred for another 1.5 hours at this temperature to remove remaining gases.

After degassing the mixture is cooled to 20° C. and pH is adjusted again to 5.0 with sodium hydroxide solution (32%). 562.1 g (31.2 mol) water are added and the mixture is stirred for 30 min.

The solid is then isolated by filtration and washed once with water (562 g) (suspension washing) and once with methanol (634 g) (displacement washing) and subsequently dried in vacuo (5 mbar) at 50° C.

The isolated product has a 99.9% purity and was obtained in 91.7% yield of theory based on DCIT-chloride.

After filtration the aqueous phase is neutralized and diluted with water for disposal.

The total liquid waste is about 13.2 kg/kg Isotianil.

Example 5

The reaction vessel is charged with 401.6 g (4.35 mol) toluene at room temperature.

190.0 g (1.37 mol) of anthranilamide are added.

Subsequently 304.4 g (1.24 mol/purity 88.4%) of 3,4-dichloroisothiazole-5-carbonyl chloride in 18.2 g toluene are added dropwise over a period of 3 hours at 85° C. The mixture is stirred at 85° C. for another 16 hours. The mixture is cooled to 16° C. and then, while cooling, 409.7 g (5.59 mol) DMF is added dropwise over a period of 30 min.

The mixture is cooled to 16° C. and 202.1 g (1.70 mol) of thionyl chloride are then added dropwise at 18° C.-23° C. over a period of 2 hours. The mixture is stirred at 18° C.-23° C. for another 2 hours.

Work-Up 536.8 g (4.29 mol) of sodium hydroxide solution (32%) and 537.4 g (29.8 mol) water are charged in a reaction vessel at room temperature and then cooled to 0° C. The reaction mixture is added over 4 hours to the sodium hydroxide solution with temperature control at a temperature between 0° C. and 25° C. and then stirred for another 30 min at this temperature.

pH after completed addition is at about pH 2.5. The resulting suspension is heated to 55° C. over a period of 2 hours and stirred for another 1.5 hours at this temperature to remove remaining gases.

After degassing the mixture is cooled to 20° C. and pH is adjusted to 5.0 with sodium hydroxide solution (32%) (0.83 mol, 104 g).

Subsequently the solid is then isolated at room temperature by filtration and washed once with water (537 g) (suspension washing) and once with methanol (606 g) (displacement washing) and subsequently dried in vacuo (5 mbar) at 50° C.

The isolated product has a 99.9% purity and was obtained in 90.9% yield of theory based on DCIT-chloride.

After filtration the aqueous phase is neutralized and diluted with water for disposal.

The total liquid waste is about 12.6 kg/kg Isotianil.

Example 6

The reaction vessel is charged with 403.5 g (3.58 mol) chlorobenzene at room temperature.

161.0 g (1.16 mol) of anthranilamide are added.

Subsequently 300.0 g (1.13 mol/purity 81.2%) of 3,4-dichloroisothiazole-5-carbonyl chloride in 42 g toluene are added dropwise over a period of 2 hours at 85° C. The mixture is stirred at 85° C. for another 2 hours. The mixture is cooled to 16° C. and then, while cooling, 370.9 g (5.06 mol) DMF is added dropwise over a period of 30 min.

The mixture is cooled to 16° C. and 168.1 g (1.41 mol) of thionyl chloride are then added dropwise at 18° C.-23° C. over a period of 2 hours. The mixture is stirred at 18° C.-23° C. for another 2 hours.

Work-Up 492.28 g (3.94 mol) of sodium hydroxide solution (32%) and 537.4 g (29.8 mol) water are charged in a reaction vessel at room temperature and then cooled to 0° C., The reaction mixture is added over 2 hours to the sodium hydroxide solution with temperature control at a temperature between 0° C. and 25° C. and then stirred for another 30 min at this temperature.

pH after completed addition is at about pH 2.9. pH is adjusted to 5.0 with sodium hydroxide solution (32%) (0.87 mol, 109 g).

The resulting mixture is heated to 55° C. over a period of 2 hours and stirred for another 1.5 hours at this temperature to remove remaining gases.

After degassing the mixture is cooled to 20°, 486.5 g (27 mol) water are added and the mixture is stirred for 30 minutes at room temperature.

Subsequently the solid is then isolated at room temperature by filtration and washed once with water (487 g) (suspension washing) and once with methanol (549 g) (displacement washing) and subsequently dried in vacuo (5 mbar) at 50° C.

The isolated product has a 98.9% purity and was obtained in 85.1% yield of theory based on DCIT-chloride.

After filtration the aqueous phase is neutralized and diluted with water for disposal.

The total liquid waste is about 16.4 kg/kg Isotianil.

The invention claimed is:

1. A process for preparing 3,4-dichloro-N-(2-cyanophenyl)-5-isothiazolecarboxamide of formula (I)

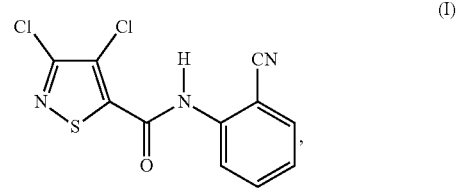 [SMILES: N#Cc1ccccc1NC(=O)c1snc(Cl)c1Cl]

by (a) reacting in an organic solvent selected from the group consisting of toluene, o-xylene, m-xylene, and p-xylene, 3,4-dichloroisothiazole-5-carbonyl chloride of formula (II)

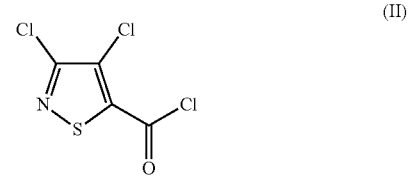

with anthranilamide of formula (III)

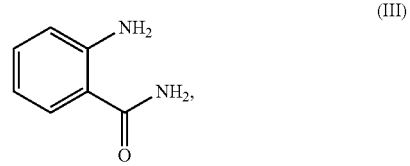

and (b) subsequently dehydrating N-[2-(aminocarbonyl)phenyl]-3,4-dichloro-5-isothiazolecarboxamide of formula (IV)

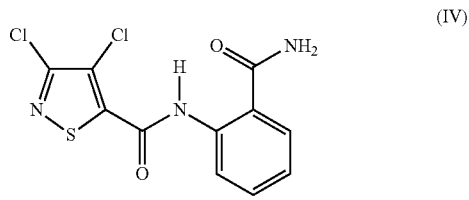 [SMILES: NC(=O)c1ccccc1NC(=O)c1snc(Cl)c1Cl]

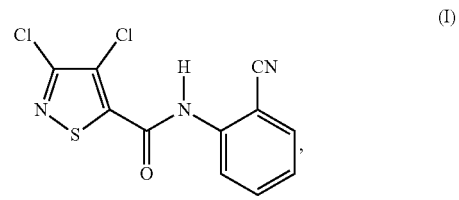 [SMILES: N#Cc1ccccc1NC(=O)c1snc(Cl)c1Cl]

by
(a) reacting in an organic aromatic solvent 3,4-dichloroisothiazole-5-carbonyl chloride of formula (II)

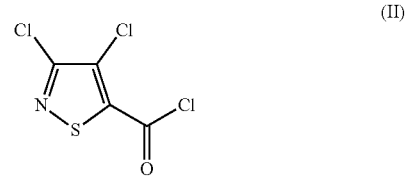

with anthranilamide of formula (III)

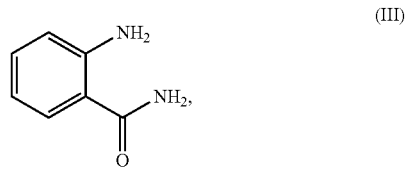

to produce N-[2-(aminocarbonyl)phenyl]-3,4-dichloro-5-isothiazole-carboxamide of formula (IV),

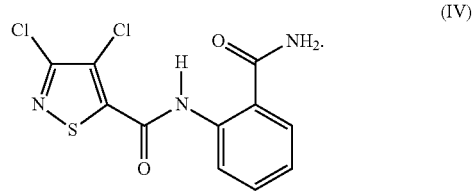 [SMILES: NC(=O)c1ccccc1NC(=O)c1snc(Cl)c1Cl]

(b) subsequently dehydrating N-[2-(aminocarbonyl)phenyl]-3,4-dichloro-5-isothiazole-carboxamide of formula (IV),
wherein (b) is carried out without isolation of N-[2-(aminocarbonyl)phenyl]-3,4-dichloro-5-isothiazolecarboxamide of formula (IV)
(c) aqueous work-up with an inorganic base (quenching), with optional adjustment of pH,
(d) degassing of quenched reaction mixture,
(e) adjustment of pH of the reaction mixture, and
(f) filtration and isolation of the product,
wherein the organic aromatic solvent is selected from the group consisting of benzene, toluene, o-xylene, m-xylene and p-xylene, and,
(a) is carried out in a range of 105-115° C., and
(b) is carried out in the presence of a dehydrating agent in a range of 16° C. to 30° C.,
wherein the dehydrating agent is a mixture of dimethylformamide and thionylchloride, with a dehydrating agent, wherein (b) is carried out without isolation of N-[2-(aminocarbonyl)phenyl]-3,4-dichloro-5-isothiazolecarboxamide of formula (IV),
wherein the workup comprises
(c) aqueous work-up with an inorganic base (quenching),
(d) degassing of the quenched reaction mixture,
(e) adjustment of pH of the reaction mixture, and
(f) filtration and isolation of the product,
wherein an acid acceptor is not present in (a).

2. The process according to claim 1, wherein (a) and (b) are carried out in toluene.

3. The process according to claim 1, wherein (a) is carried out at a temperature in the range between 20° C. to 160° C.

4. The process according to claim 1, wherein (a) is carried out at a temperature in a range from the boiling point of the respective solvent used in the process to 10K above said boiling point.

5. The process according to claim 1, wherein a reagent used as dehydrating agent in (b) is selected from the group consisting of mixtures of dialkylformamide with thionyl chloride, phosphorus oxychloride, phosgene and/or chloromethylenedimethylammonium chloride.

6. The process according to claim 5, wherein the amounts of phosgene or thionyl chloride employed in (b) are between 1 and 2.5 mol per mole of 3,4-dichloroisothiazole-5-carbonyl chloride.

7. The process according to claim 5, wherein the amounts of dialkylformamide employed in (b) are between 1.0 and 8.0 mol per mole of 3,4-dichloroisothiazole-5-carbonyl chloride.

8. The process according to claim 1, wherein the base used in the workup of (c) is selected from the group consisting of carbonate or hydroxides of alkali or earth alkali metals.

9. The process according to claim 1, wherein in (c) the pH is adjusted to a pH between 1.0 and 6.0.

10. The process according to claim 1, wherein the mixture after addition of the base in (c) is heated to 50° C. 60° C., and stirred at that temperature over a period of 2.0 to 4.0 h for degassing.

11. The process according to claim 1, wherein the pH after degassing is adjusted to a pH between 5 and 7.

12. The process according to claim 1, wherein (a) is carried out under reduced pressure and the temperature is in a range from the boiling point under said pressure of the respective solvent used in the process to 10K above said boiling point.

13. The process according to claim 12, wherein (a) is carried out under reduced pressure, wherein the pressure is in a range from 10 mbar to 700 mbar.

14. A process for preparing 3,4-dichloro-N-(2-cyanophenyl)-5-isothiazolecarboxamide of formula (I)

wherein the amount of thionyl chloride is between 1.0 and 1.5 mol per mole of 3,4-dichloroisothiazole-5-carbonyl chloride, and wherein the amount of dimethylformamide is between 4.0 and 5.0 mol per mole of 3,4-dichloroisothiazole-5 carbonyl chloride, and wherein (c) comprises addition of a 32% solution of sodium hydroxide, wherein the amount of sodium hydroxide is between 1.8 and 2.2 mol per mole of thionyl chloride, wherein the pH after quenching is between 1.8 and 2.2, wherein the reaction mixture is added to the base over a period of time of 2 hours under temperature control, wherein the temperature is allowed to increase to a range from 50° C. to 60° C., and wherein in (d) volatile reaction products are removed from the reaction mixture by degassing over a period of 2 to 4 h at 55° C., and wherein in (e), the temperature is adjusted to 20° C. to 22° C. and then the pH is adjusted to a pH in the range between 5 and 6 with a 32% solution of sodium hydroxide, and wherein the precipitated product is filtered off and washed with water and methanol.

15. The process according to claim 5, wherein the amounts of phosgene or thionyl chloride employed in (b) are between 1 and 1.3 mol per mole of 3,4-dichloroisothiazole-5-carbonyl chloride.

16. The process according to claim 5, wherein the amounts of dialkylformamide employed in (b) are between 4.3 and 4.7 mol per mole of 3,4-dichloroisothiazole-5 carbonyl chloride.

17. The process according to claim 1, wherein the base used in the workup of (c) is selected from the group consisting of sodium carbonate, potassium carbonate, sodium hydroxide, and potassium hydroxide.

18. The process according to claim 1, wherein in (c) the pH is adjusted to a pH between 1.8 and 2.2.

19. The process according to claim 1, wherein the mixture after addition of the base in (c) is heated to 50° C.-60° C. and stirred at that temperature over a period of 1.0 h to 2.5 h-for degassing.

20. The process according to claim 12, wherein the process (a) is carried out under reduced pressure, wherein the pressure is in a range from 200 mbar to 400 mbar.

\* \* \* \* \*